United States Patent [19]
Coleman

[11] Patent Number: 5,376,804
[45] Date of Patent: Dec. 27, 1994

[54] OPTICAL ANALYSIS SYSTEM AND POSITIONING APPARATUS THEREOF

[75] Inventor: Clive I. Coleman, London, England

[73] Assignee: GEC-Marconi Limited, Middlesex, United Kingdom

[21] Appl. No.: 90,071

[22] PCT Filed: Dec. 2, 1992

[86] PCT No.: PCT/GB92/02239
§ 371 Date: Jul. 19, 1993
§ 102(e) Date: Jul. 19, 1993

[87] PCT Pub. No.: WO93/11469
PCT Pub. Date: Jun. 10, 1993

[30] Foreign Application Priority Data
Dec. 2, 1991 [GB] United Kingdom ............... 9125603

[51] Int. Cl.$^5$ .................................... G01N 21/86
[52] U.S. Cl. .................. 250/548; 250/201.2
[58] Field of Search ........... 250/548, 571, 201.2, 250/201.4, 201.7; 356/400, 401

[56] References Cited
U.S. PATENT DOCUMENTS
3,989,385 11/1976 Dill et al. ..................... 250/548
5,148,036 9/1992 Matsugu et al. ............... 356/401

FOREIGN PATENT DOCUMENTS
0131098 1/1985 European Pat. Off. .
1138128 12/1968 United Kingdom .
1375439 11/1974 United Kingdom .
1421666 1/1976 United Kingdom .
1509574 5/1978 United Kingdom .

Primary Examiner—David C. Nelms
Attorney, Agent, or Firm—Kirschstein Ottinger, Israel & Schiffmiller

[57] ABSTRACT

An optical analysis or processing system for use, for example, in the analysis of microscopic spots of material by their effect on a very fine polarized beam of light (e.g., FPIA). For multiple "spot" analysis the spot samples are disposed on a substrate in predetermined relation with an optical pattern, bars, chevrons, etc. The substrate is mounted in the path of the fixed and focused beam with three degrees of freedom of movement. A video camera records the optical pattern very accurately and controls the substrate mounting to position a selected sample spot at the beam focus. Multiple and rapid sample analysis can thus be performed.

16 Claims, 2 Drawing Sheets

OPTICAL ANALYSIS SYSTEM AND POSITIONING APPARATUS THEREOF

BACKGROUND OF THE INVENTION

1. Field of the Invention

This invention relates to an optical analysis system, particularly but not exclusively suited to automated analysis of large numbers of samples, and further, to a positioning apparatus for the samples of such a system.

2. Description of the Related Art

For many clinical, forensic or other applications, it is required to perform fluorescence/polarization (FPIA) or other optical analyses on large quantities of samples, which may individually be very small "microspots".

The microspots may be typically a few tens of micrometres in diameter, and may need to be aligned with a fluorescent probe, and focussed to similar tolerances. While it is feasible to align and bring into focus a small number of samples manually, (e.g. using an adjustable stage viewed through a microscope) there is a need for a rapid method of achieving this automatically.

SUMMARY OF THE INVENTION

One object of the present invention is to provide an optical analysis system and positioning apparatus which facilitates such multiple sample analysis.

According to the present invention positioning apparatus for indexing a stage to align selectively a plurality of locations on the substrate with a focus of optical test or processing means, comprises a mounting arrangement for the substrate permitting at least two degrees of freedom of the substrate in its own plane, the substrate having on its surface an optical location, orientation and focusing pattern with at least part of which the locations have a predetermined spatial relationship, the mounting arrangement further permitting movement of the substrate in a direction transverse to its own plane, the positioning apparatus further including means so arranged in relation to the optical test or processing means as to have a common focus with the test or processing means, the imaging means having image storage means for storing at least part of an image of the location, orientation and focusing pattern and focus assessment means for assessing the position relative to the common focus of at least part of the location, orientation and focusing pattern, the apparatus further comprising control means for controlling the mounting arrangement in response to the relative disposition of live and stored images of the substrate and in response to the focus assessment means.

The imaging means preferably includes a digital data processor responsive to the disposition of a live image of the optical pattern to control the mounting arrangement to move the substrate to a position in which a selected location lies at the common focus.

The optical pattern may comprise a location and orientation reference pattern and a separate focusing pattern.

The processor may control the mounting arrangement to index the substrate through the locations successively.

The processor is preferably responsive to the imaging means to control the mounting arrangement to maximise the contrast between different parts of the image of the focusing pattern.

The optical reference pattern may identify both position and orientation on the substrate.

According to a feature of the invention, an optical analysis system may comprise positioning apparatus as aforesaid, the substrate being adapted to carry test samples at each of the locations.

BRIEF DESCRIPTION OF THE DRAWINGS

One embodiment of an optical analysis system and positioning apparatus for such a system will now be described, by way of example only, with reference to the accompanying drawings, of which.

DETAILED DESCRIPTION OF THE PREFERRED EMBODIMENTS

Figure 1:
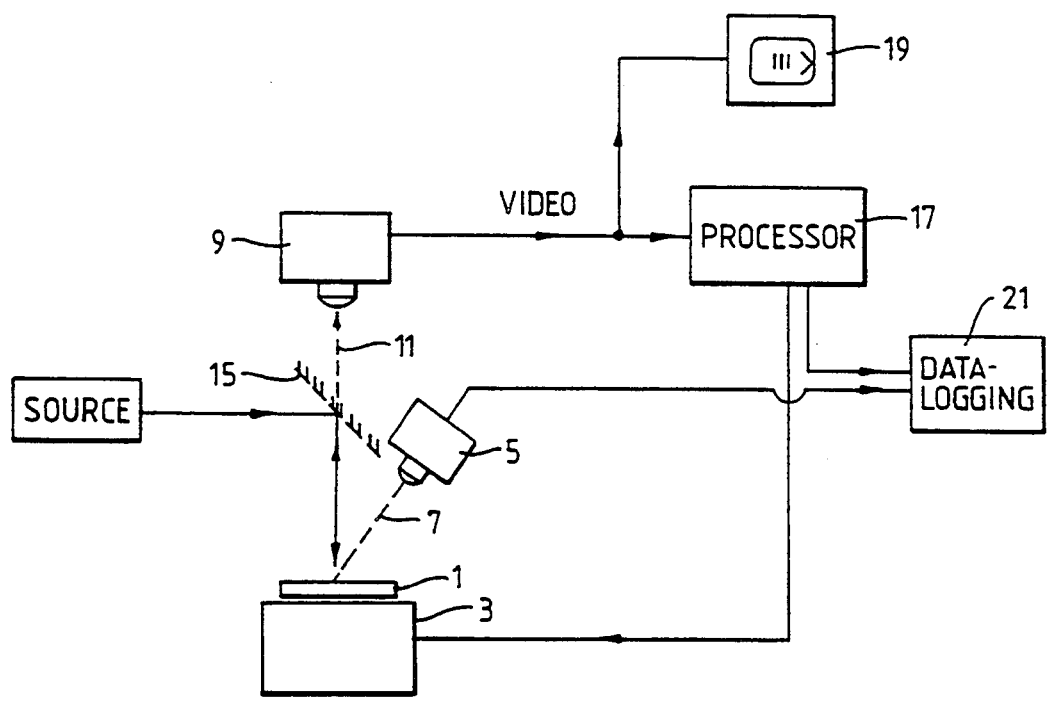
FIG. 1 is a diagram of the overall system.

Referring to FIG. 1, a substrate 1 is carried by a mounting arrangement 3. The substrate 1 will be described subsequently but basically consists of a disc, plate or platform on which, in one application, samples for analysis are deposited. It will become clear that the nature and thickness of the substrate are not relevant to the invention and the term "substrate" is to be interpreted in this broad sense. In other applications the substrate 1 might be a platform having a plurality of point locations at each of which some process was required.

In the present case the samples are analysed by an optical analysis unit 5 which may, for example, be such as is employed in known fluorescence polarization immunoassay (FPIA) testing. In this system a material to be detected (e.g. a drug) is labelled with a fluorescent dye which effects the polarization plane of an incident light beam; the 'tracer-drug' thus produced is made to compete with the suspect material (suspected of being the same drug) for locking engagement with an antibody material. A beam of polarized light incident on combination of reagents has its polarization plane rotated to a degree dependent on the proportions of suspect material and tracer drug that have locked to the antibody. Such analysis systems are known and do not form part of the present invention. The important point is that a very narrow beam from the unit 5 is required to be focused on to a substantially point location on the substrate carrying a microspot of the the reagent combination in the above drug detection case . It is assumed that the optical unit 5 has a fixed focus on its axis 7 and it is therefore required to position each deposit selectively or in sequence at this focus.

A video camera 9 having an optical axis 11 is set with a fixed focus arranged to coincide with the plane of the substrate 1 when the substrate 1 is properly positioned for the optical unit 5. The substrate is then illuminated by a light source 13 by way of a partially transparent mirror 15.

The video camera produces a live image which is applied to a combined video and digital data processor 17 which controls the mounting 3 of the sample substrate as will be explained.

A monitor 19 may also be coupled to the video camera output for manual operation of the system or for pure monitoring of the automated process.

The actual individual sample test results from the unit 5 are stored in a data logger 21, correlated with information from the processor 17 as to the identity of the sample.

Operation of the system requires the sample substrate to be indexed from one sample to the next, either in sequence or by selection, and, at each location the sample has to be brought accurately to the focus of the optical unit 5. For this purpose the mounting arrangement 3 has to have at least two degrees of freedom for moving the substrate in its own plane. These may be 'X' and 'Y' translational movements or angle (rotational) and radius (translational) movements, or a combination of both. There is then a further requirement for movement of the substrate with at least a component along the axis 7 of the optical unit.

Figure 2:
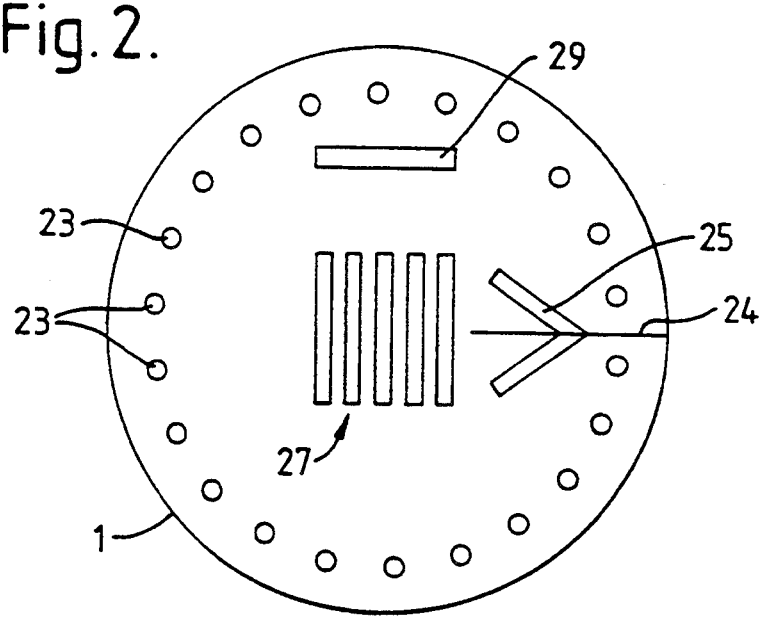
FIGS. 2 and 3 are plan views of alternative sample carrying substrates.

Referring now to FIG. 2, this shows one example of a substrate carrying samples for analysis. The samples 23 are regularly spaced around the periphery of the substrate, ie concentrically with the circular substrate 1. The substrate, which may consist of a polystyrene or ceramic disc, carries an optical reference pattern 25 which uniquely identifies a particular radius 24 of the disc. In the example shown, the reference pattern 25 is a chevron but any pattern is suitable which provides the unique radius identification, for example two (different) peripheral marks at each end of a diameter. It is necessary of course that in this case the ends of a diameter are distinguishable one from the other. It is also desirable that the reference pattern extends over a considerable part of a diameter for greaser accuracy in positioning.

In addition to the reference pattern 25 the substrate carries a focusing pattern 27. This consists of a row of bars which are imaged by the video camera 9 and passed to the control processor 17 for maximisation of the contrast in the image. The bar pattern 27 has a bar width and spacing which are large enough to be easily resolvable by the camera so that the imaging system and processor 17 can distinguish each bar from the next. The bars are also sufficiently close that when the substrate is out of the camera focal plane to the maximum likely extent the image of one bar touches or overlaps the next. The control processor includes means for assessing the contrast of the focusing pattern. This may be done by scanning across a stored image of the bars in the processor and detecting the peak/trough signal ratio. This signal will of course be a maximum when there is at least some 'all-white' image between the bars and if the bars are sufficiently close this condition will obtain for a very limited axial range of the camera.

The focus indication from the processor 17 then controls the axial movement of the substrate, ie movement along the axis 11, until focus is achieved. Lateral alignment of an individual sample with the axis 7 is achieved from stored information as to the location of the sample referred to the chevron 25 and the substrate periphery. Thus the radius and/or distance-from-the-substrate-edge of a sample is known, together with the angle offset from the chevron radius. The substrate is thus moved, either by angle and radius or in X and Y coordinates, until the video camera image of the chevron 25 and substrate periphery accord with the stored information.

With the focal bar pattern (27) shown, it will generally be more convenient to orient the substrate to accord with the stored image before performing the focus assessment. In an alternative focus pattern the bars may be concentric rings, around the periphery for convenience. The scan of the processor store, for contrast assessment, may then be performed at a fixed store location.

The substrate may be one of a large number and it is convenient to include a serial number code 29 as part of the overall markings. This code may be a decimal number requiring decoding by the processor, or a binary or other code. It may be convenient to incorporate this serial number block as part of (or all of) the lateral reference pattern otherwise provided by the chevron 25. It is only necessary to arrange it in such a position as to indicate a unique radius.

It would also be possible to combine the functions of the lateral reference pattern 25 and the focus (axial) pattern 27. For example, the bars shown could be of decreasing length from left to right, the lengths being accurately defined so that an imaginary line of symmetry through them pointed to a unique peripheral point. Again, merely by moving the bar pattern bodily to the right (say), its line of symmetry would indicate such a unique point.

The substrate itself is conveniently, as mentioned above, a polystyrene or ceramic disc and the markings may be impressed by standard photoetching, laser-marking or other appropriate techniques.

Figure 3:
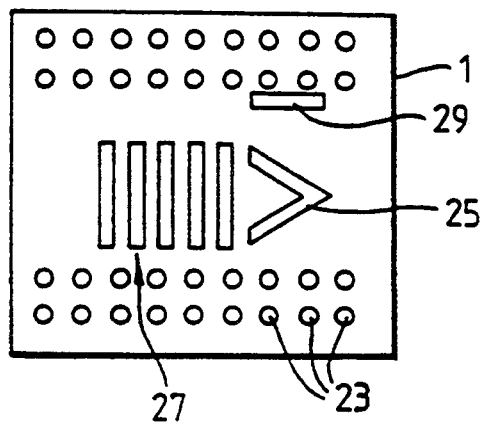

FIG. 3 shows an alternative sample substrate of rectangular form. In this case the samples are deposited in rows parallel to the long edges and symmetrically disposed about a centre line. Again, the substrate has focusing and lateral reference patterns and a serial number.

It will be clear that in the two examples shown, the form of the substrate, circular or rectangular, can be used as part of the sample location reference, ie referring the sample location to the periphery. In an alternative arrangement the peripheral form of the substrate may be ignored and a complete lateral reference provided by markings. In the substrates shown, the chevron itself could be used to indicate both position and orientation if it is sufficiently well defined. Alternatively, for example, three widely-spaced spot markings forming an isosceles triangle could be used for both position and orientation references.

For use in an immunoassay application as described above, the antibody would be deposited at the point location on the substrate in preparation for later application of the competing antigens. Both of these operations are performed using the above described machine vision system to orientate, locate and focus the substrate. The reagents are deposited preferably in a predetermined orientation relative to the chevron but otherwise in a recorded orientation. The circular nature of the substrate in FIG. 2 facilitates the mechanical operation of the system.

The substrate is placed on the mounting arrangement and initially the chevron radius aligned with a datum (say the axis 7) by the processor. The analysis sequence is then set in motion, the processor bringing each sample in turn on to the axis 7 and at each such indexing the processor makes a focus assessment and correction. After each analysis the sample data, including sample characteristics, identity, location, substrate identity, is output to the data logger.

I claim:

1. Positioning apparatus for indexing a substrate to align selectively a plurality of locations on the substrate with a focus of optical test or processing means, the apparatus comprising a mounting arrangment for the substrate permitting at least two degrees of freedom of the substrate in its own plane, the substrate having on its surface an optical location, orientation and focusing pattern with at least part of which said locations have a predetermined spatial relationship, said mounting arrangement further permitting movement of said substrate in a direction transverse to its own plane, the positioning apparatus further including imaging means so arranged in relation to said optical test or processing means as to have a common focus with the test or processing means, said imaging means having image storage means for storing at least part of an image of said location, orientation and focusing pattern and focus assessment means for assessing the position relative to said con,non focus of at least part of said location, orientation and focusing pattern, the apparatus further comprising control means for controlling said mounting arrangement in response to the relative disposition of live and stored images of said substrate and in response to said focus assessment means.

2. Positioning apparatus according to claim 1, wherein said imaging means includes a digital data processor responsive to the disposition of a said live image of said optical pattern to control said mounting arrangement to move the substrate to a position in which a selected said location lies at said common focus.

3. Positioning apparatus according to claim 1, wherein said optical pattern comprises a location and orientation reference pattern and a separate focusing pattern.

4. Positioning apparatus according to claim 1, wherein said processor controls said mounting arrangement to index the substrate through said locations successively.

5. Positioning apparatus according to claim 3, wherein said processor is responsive to said imaging means to control said mounting arrangement to maximise the contrast between different parts of the image of said focusing pattern.

6. Positioning apparatus according to claim 1, wherein said substrate is circular and said locations are regularly spaced in a circle concentric with the substrate periphery, said optical reference pattern indicating a unique radius on the substrate.

7. Positioning apparatus according to any of claims 1 to 5, wherein said substrate is rectangular and said locations are regularly spaced in rows symmetrically about a centre-line of the rectangle, said optical reference pattern indicating a particular edge of the stage.

8. Positioning apparatus according to any of claims 1 to 5, wherein said optical reference pattern identifies both position and orientation on the stage.

9. Positioning apparatus according to claim 3, wherein said focusing pattern comprises a plurality of discrete marks of such dimensions and spacing as to be easily resolved by said imaging means.

10. Positioning apparatus according to claim 9, wherein said focusing pattern comprises a plurality of spaced apart parallel bars.

11. Positioning apparatus according to claim 9, wherein said focusing pattern comprises a plurality of concentric rings.

12. An optical analysis system comprising positioning apparatus according to claim 1, wherein said substrate is adapted to carry test samples at each of said locations.

13. An optical analysis system according to claim 12, wherein said imaging means includes a video camera.

14. An optical analysis system according to claim 13, wherein said processor and said optical test means are coupled to a data logger to record the test result and sample identity for each sample.

15. An optical analysis system according to claim 13, wherein a light source is arranged to illuminate said substrate substantially normally by way of a partially transparent mirror positioned between said video camera and said substrate.

16. An optical analysis system according to claim 10 wherein said processor is adapted selectively for manual indexing of the substrate.

* * * * *